(12) United States Patent
Keshavarzian et al.

(10) Patent No.: US 10,222,370 B2
(45) Date of Patent: Mar. 5, 2019

(54) SCREENING ASSAY FOR CHOICE OF PREBIOTIC TO PREVENT/TREAT GASTROINTESTINAL AND SYSTEMIC DISEASES

(71) Applicants: Rush University Medical Center, Chicago, IL (US); Purdue Research Foundation, West Lafayette, IN (US)

(72) Inventors: Ali Keshavarzian, Evanston, IL (US); Sander de Kivit, Chicago, IL (US); Bruce Hamaker, West Lafayette, IN (US)

(73) Assignees: Rush University Medical Center, Chicago, IL (US); Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 15/302,103

(22) PCT Filed: Apr. 6, 2015

(86) PCT No.: PCT/US2015/024486
§ 371 (c)(1),
(2) Date: Oct. 5, 2016

(87) PCT Pub. No.: WO2015/157163
PCT Pub. Date: Oct. 15, 2015

(65) Prior Publication Data
US 2017/0184569 A1   Jun. 29, 2017

Related U.S. Application Data
(60) Provisional application No. 61/976,118, filed on Apr. 7, 2014.

(51) Int. Cl.
*C12Q 1/02*        (2006.01)
*G01N 33/50*       (2006.01)
(Continued)

(52) U.S. Cl.
CPC .......... *G01N 33/5044* (2013.01); *C12N 1/20* (2013.01); *G01N 33/5041* (2013.01);
(Continued)

(58) Field of Classification Search
CPC .................................................... C12Q 1/025
See application file for complete search history.

(56) References Cited

U.S. PATENT DOCUMENTS

| | | |
|---|---|---|
| 8,486,668 B2 | 7/2013 | Ritter et al. |
| 2007/0196890 A1 | 8/2007 | Vulevic et al. |

(Continued)

FOREIGN PATENT DOCUMENTS

| | | |
|---|---|---|
| WO | WO 2010/023422 A1 | 3/2010 |
| WO | WO 2012/118799 A2 | 9/2012 |

OTHER PUBLICATIONS

Acosta-Martinez, V. et al.; "Tag-encoded pyrosequencing analysis of bacterial diversity in a single soil type as affected by management and land use"; Soil Biology & Biochemistry, vol. 40; pp. 2762-2770; Nov. 30, 2008.

(Continued)

*Primary Examiner* — Rosanne Kosson
(74) *Attorney, Agent, or Firm* — Brinks Gilson & Lione

(57) ABSTRACT

An assay and a method for identifying a prebiotic to treat a subject in need thereof to promote intestinal barrier integrity or to blunt an inflammatory response are provided.

15 Claims, 7 Drawing Sheets

(51) Int. Cl.
*C12N 1/20* (2006.01)
*G01N 33/68* (2006.01)

(52) U.S. Cl.
CPC ..... *G01N 33/6863* (2013.01); *G01N 33/6866* (2013.01); *G01N 33/6869* (2013.01); *G01N 2333/195* (2013.01); *G01N 2333/52* (2013.01)

(56) References Cited

U.S. PATENT DOCUMENTS

| 2011/0281762 A1 | 11/2011 | Sonnenburg et al. | |
|---|---|---|---|
| 2011/0301249 A1* | 12/2011 | Challakere | C12N 5/0601 514/777 |

OTHER PUBLICATIONS

Ter Braak, C.J.F. et al.; CANOCO Reference Manual and CanDraw for Windows User's Guide: Software for Canonical Community Ordination (version 4.5); Microcomputer Power, Ithaca, NY, USA; 500 pages; 2002.

Clarke, K.R. et al.; Change in Marine Communities: An Approach to Statistical Analysis and Interpretation, 2nd Edition; Plymouth Marine Laboratory, UK: Primer-E Ltd.; 176 pages; 2001.

Cole, J.R. et al.; "The Ribosomal Database Project: improved alignments and new tools for rRNA analysis"; Nucleic Acids Research, vol. 37, Database issue; pp. D141-D145; Nov. 12, 2008.

Edgar, R.C.; "Search and clustering orders of magnitude faster than BLAST"; Bioinformatics, vol. 26, No. 19; pp. 2460-2461; Oct. 1, 2010.

Gontcharova, V. et al.; "Black Box Chimera Check (B2C2): a Windows-Based Software for Batch Depletion of Chimeras from Bacterial 16S rRNA Gene Datasets"; The Open Microbiology Journal, vol. 4; pp. 47-52; Nov. 8, 2010.

Ishak, H.D. et al.; "Bacterial Diversity in *Solenopsis invicta* and *Solenopsis geminata* Ant Colonies Characterized by 16S amplicon 454 Pyrosequencing"; Microbial Biology, vol. 61, Issue 4; pp. 821-831; Jan. 18, 2011.

De Kivit, S. et al.; "Apical TLR ligation of intestinal epithelial cells drives a $T_h1$-polarized regulatory or inflammatory type effector response in vitro"; Immunobiology, vol. 216; pp. 518-527; Apr. 30, 2011.

De Kivit, S.; Restoring mucosal tolerance by non-digestible oligosaccharides under inflammatory conditions; ISBN 978-90-9027337-2; Chapter 3, pp. 51-72, p. 52, Abstract, p. 64; 2013.

Lebet, V. et al.; "Measurement of Fermentation Products and Substrate Disappearance During Incubation of Dietary Fibre Sources with Human Faecal Flora"; LWT—Food Science and Technology, vol. 31, Issue 5; pp. 473-479; Aug. 1998.

McDonald, D. et al.; "The Biological Observation Matrix (BIOM) format or: how I learned to stop worrying and love the ome-ome"; GigaScience, vol. 1, No. 7; Jul. 12, 2012.

Rose, D.J. et al.; "Starch-entrapped microspheres show a beneficial fermentation profile and decrease in potentially harmful bacteria during in vitro fermentation in faecal microbiota obtained from patients with inflammatory bowel disease"; British Journal of Nutrition, vol. 103; pp. 1514-1524; May 1, 2010.

International Search Report dated Jun. 29, 2015 for International Application No. PCT/US2015/024486.

* cited by examiner

SCREENING ASSAY FOR CHOICE OF PREBIOTIC TO PREVENT/TREAT GASTROINTESTINAL AND SYSTEMIC DISEASES

This application claims the benefit under 35 U.S.C. § 371 of International Application No. PCT/US2015/024486, filed Apr. 6, 2015, which claims the benefit of US Provisional Application No. 61/976,118, filed Apr. 7, 2014, which are incorporated by reference herein in their entirety.

RELATED APPLICATIONS

This application claims the benefit of U.S. Provisional Application No. 61/976,118, filed Apr. 7, 2014, which is incorporated by reference herein in its entirety.

BACKGROUND

A method and assay for screening panel of prebiotic products to identify the most suitable product for prevention and/or treatment of a specific disorder that is associated with poor gut health is described. Poor gut health can be broadly defined as gut leakiness and/or dysbiosis and/or inflammation and/or other specific indications in a given subject that can be managed, in part, through the use of a prebiotic. Based on the indication, the method provides the opportunity to personalize a prebiotic formulation for use to manage, control or alleviate poor gut heath. The screening assay allows for identifying the appropriate prebiotic or a combination of prebiotics for an individual patient with intestinal and systemic diseases where gut initiated inflammation, dysbiosis [abnormal intestinal microbiota composition] and gut leakiness are key for initiation and/or progression of the disease. Appropriateness of the prebiotic is based on the effects of the prebiotic on the intestinal microbiota composition and fermentation products to promote gut health that may be defined by improved intestinal barrier-less gut leakiness and increased number of probiotic bacteria/less pathogenic bacteria and increased amount of short chain fatty acids like butyrate as well as blunted inflammatory response that may be defined by less production of pro-inflammatory cytokines by their PBMC.

Recent studies have shown that abnormal microbiota composition [dysbiosis] are linked to many intestinal and systemic inflammatory disorders, including food allergy, chronic inflammatory bowel disease (IBD) (i.e. ulcerative colitis and Crohn's disease), HIV, irritable bowel syndrome, diverticular diseases, *Clostridium Difficile* colitis, alcoholic liver disease, non-alcoholic steatohepatitis (NASH), and even metabolic syndrome and obesity, and neurological disorders like Parkinson's disease, autism and Alzheimer's disease. Furthermore, it is now well established that intestinal microbiota regulate intestinal epithelial barrier function and therefore changes in intestinal microbiota composition not only can promote local and systemic inflammation by producing excessive amounts of pro-inflammatory factors like endotoxins but also can compromise intestinal barrier function (leaky gut) and increase exposure of intestinal and systemic immune systems to these pro-inflammatory factors causing sustained and inappropriate inflammatory response that could lead to above mentioned inflammatory diseases. Thus, intervention to correct dysbiotic intestinal microbiota composition and improve intestinal barrier function could prevent and/or treat these disorders.

Prebiotics are capable of changing microbiota composition and promoting intestinal barrier integrity. Prebiotics are poorly absorbed carbohydrates that can reach into the colon after ingestion and are used by intestinal bacteria as a source of energy for growth. Thus, depending on the type of prebiotic product, the prebiotic product can favor or disfavor growth of specific groups of bacteria and thus are capable of changing the composition of the intestinal microbiota community and promoting health. Prebiotics have been investigated for their capacity to prevent and/or treat intestinal and systemic inflammation in both murine and human studies and their beneficial and anti-inflammatory effects have been established. For example, it has also been shown that the genomic DNA of these bacterial species can promote immunological tolerance. In addition, prebiotic oligosaccharides are fermented by specific bacterial strains present in the gut microbiota, resulting in the production of the short-chain fatty acids (SCFA) acetate, propionate and butyrate that support the barrier function of the intestinal epithelium. Indeed, supplementation of prebiotics into the diet is known to affect the gut microbiota composition. Prebiotics can favor the growth of specific bacterial strains, including *Bifidobacteria* spp, *Lactobacilli* and butyrate producing bacteria. The growth of these bacteria promotes immune tolerance and restoration of intestinal barrier integrity presumably through increased production of SCFA.

The challenge in clinical medicine is to determine the type of prebiotic product that is most suitable for a given patient or a group of patients with a specific disease because: (1) not all prebiotics are the same and the effects of the prebiotics on intestinal microbiota composition and fermentation profile is specific for a given product. Furthermore, the impact of a given prebiotic on microbiota composition, immune response and intestinal barrier integrity is highly variable among different subjects; (2) not all individual respond to a given prebiotic similarly; (3) microbiota composition is different among patients even in those with a similar disease and (4) the desired outcome from prebiotic supplementation differs and is based on pathogenesis of a given disease. For example, for some disorders promotion of immune tolerance is the priority, by way of non-limiting example, in the case of a food allergy. In others disorders, restoration of intestinal barrier integrity is the desired outcome, for example in Alzheimer's disease, Parkinson's disease and NASH. Further, in other disorders, restoration of intestinal barrier function and promotion of anti-inflammatory pathways are the key, such as IBD, but not limited thereto. Thus, a method to identify the prebiotic(s) for a given disease state and a given patient is needed to optimize the use of a prebiotic formulation. The bioassay described herein is in response to this challenge and to the clinically significant unmet need.

There is no currently available method to achieve the goal of identifying the prebiotic(s) based on a patient and a disease. The screening method described herein will respond to this unmet need and provide an opportunity to offer a personalized prebiotic treatment to patients who suffers from disorders where changes in microbiota composition and/or function has therapeutic efficacy.

BRIEF SUMMARY

An assay and a method for identifying a prebiotic for treatment of a subject in need thereof to promote intestinal barrier integrity or to blunt an inflammatory response are provided.

DETAILED DESCRIPTION

The embodiments disclosed below are not intended to be exhaustive or to limit the scope of the disclosure to the precise form in the following description. Rather, the embodiments are chosen and described as examples so that others skilled in the art may utilize its teachings.

A bioassay (FIG. 1) was developed to screen candidate prebiotic products in order to choose the one most suitable and most effective for a given patient/individual (or a group of patients/individuals) who desire to prevent and/or treat a given disorders and in order to achieve the desired outcomes, such as, but not limited to changes in microbiota composition via favoring and/or disfavoring growth of specific bacteria group; increasing production of specific short chain fatty acids (SCFA); increasing the ratio of butyrate to total SCFA 20% or more, increasing the propionate to SCFA ratio to 20% or more; restoring intestinal epithelial cell barrier integrity; promoting immune tolerance such as by increasing the percent of $T_{reg}$ in the intestinal mucosa; directing immune response to specific pathway for example from Th1 to Th2 or from Th17 to Th22. In some embodiments, examples of changes in microbiota composition include increasing the diversity index, increasing the Firmicutes/Bacteroidetes ratio above 2:1, decreasing protobacter abundance to less than 3%.

"Treating", "treat", or "treatment" within the context of the instant invention, means an alleviation of symptoms associated with a disorder or disease, or halt of further progression or worsening of those symptoms, or prevention or prophylaxis of the disease or disorder.

Figure 1:
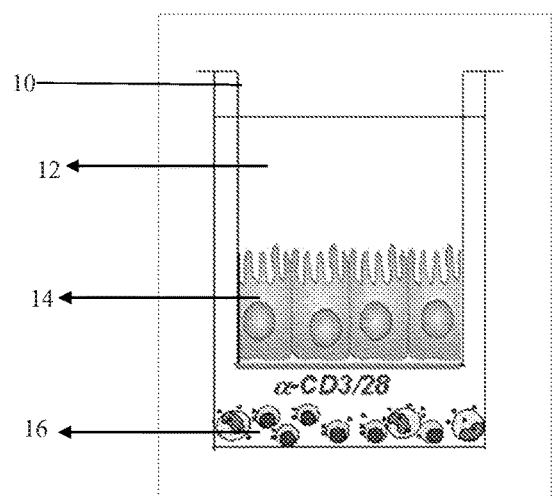
FIG. 1 shows a schematic representation of the T84/PBMC co-culture.

In the assay, as shown in FIG. 1, co-cultures of a monolayer of T84 cells 14, an intestinal epithelial cell line, with peripheral blood mononuclear cells (PBMC) 16 from a healthy volunteer are cultured in a culture dish or multi-well plate 10 with the PBMC placed on the basolateral aspect of the monolayer. The T84 cells are grown in DMEM/F-12 (1:1) supplemented with GlutaMAX®, 10% fetal bovine serum and 5 mM penicillin/streptomycin. (T84 cells (human colorectal carcinoma cell line, ATCC® CCL-248™, Manassas, Va., USA). T84 cells were seeded in 12-well transwell insert filters (Corning Inc., NY, USA) and cultured in T84 cell medium for 3-4 weeks till co-culture with PBMC. Transepithelial electrical resistance (TER) was measured during culture, which generally increases to >1500 Ω×cm² and becomes stable after 3-4 weeks of culture. When TER was ≥2000 Ω×cm², T84 monolayers 14 were co-cultured with 1.5×10⁶ PBMC 16 in the basolateral chamber.

The PBMC 16 for use in the co-cultures are isolated from 20 mL fresh blood from healthy controls (n=6) and subjects with food allergy (n=8) (Table 1). The average age of healthy controls was 36 (range 24-54) vs. 51 (range 26-74) for food allergic subjects (P>0.05). PBMC were isolated by density gradient centrifugation using lymphocyte separation medium according to manufacturer's protocol (Cellgro, Mediatec, Inc., Manassas, Va., USA). PBMC were collected in RPMI1640 supplemented with L-glutamine (Gibco), 2.5% fetal bovine serum, 1% penicillin/streptomycin and 1% sodium pyruvate (Sigma, St. Louis, Mo., USA) (PBMC medium) at 1×10⁶ cell/mL.

TABLE 1

| Patient | Positive allergen[a] | Total IgE |
|---|---|---|
| 1 | Peanut | 30 |
| 2 | Peanut, milk | N/A |
| 3 | Peanut, egg | N/A |
| 4 | Peanut, milk | 222 |
| 5 | Peanut, milk | 5 |
| 6 | Peanut | 12.5 |

TABLE 1-continued

| Patient | Positive allergen[a] | Total IgE |
|---------|----------------------|-----------|
| 7 | Peanut | 76.4 |
| 8 | Peanut | 263 |

[a]Determined by skin testing

T84/PBMC co-cultures were maintained in PBMC medium. PBMC were stimulated using CD3 and CD28 antibodies (clone OKT3 and CD28.2, 0.2 µg/mL; eBioscience, San Diego, Calif., USA) and simultaneously IEC were stimulated apically with Pam3CSK4, LPS or type C CpG oligonucleotide M362 (Invivogen, San Diego, Calif., USA) as previously described [9]. Cultures were maintained at 37° C./5% $CO_2$ for indicated time points.

The barrier integrity of T84 monolayers was assessed by measuring the TER and paracellular permeability to 4 kDa FITC-dextran. In short, TER was measured using a dual electrode system designed for cell culture insert analysis (EVOM; World Precision Instruments, Sarasota, Fla.) prior to co-culture and at indicated time points during co-culture. Data is reported as percentage of the initial TER value measured before co-culture. For assessment of permeability, T84 monolayers were separated from PBMC and cultured in PBMC medium for 1 h. The monolayers were then apically exposed to 1 mg/mL 4 kDa FITC-dextran (Sigma) and basolateral supernatants were collected after 60 min. FITC-dextran was measured at excitation wavelength 485 nm and emission wavelength 520 nm. The 4 kDa FITC-dextran flux was expressed as $pmol/(h \times cm^2)$.

Cytokine levels were measured by ELISA. IL-6, IL-8, IL-10, IL-13, IFN-γ and TNF-α were measured using the Ready-Set-Go!® ELISA kit from eBioscience according to manufacturer's protocol (eBioscience, Inc., San Diego, Calif., USA).

The data are represented as mean±SEM. $P<0.05$ was considered statistically significant. Comparison between healthy and food allergic subjects was done by using unpaired Student's t test. Evaluation of TLR stimulation was done using one-way ANOVA for repeated measurements followed by Dunnett's post hoc test. When data were not normally distributed, Mann-Whitney U test or Friedman test, followed by Dunn's multiple comparison test was performed. Data was analyzed using GraphPad Prism, version 6.0 (La Jolla, Calif., USA).

In some experiments, PBMC are stimulated using antibodies against CD3 and CD28 and T84 cell monolayers were simultaneously exposed to synthetic TLR ligands or fermentation product 12 (co-culture of stool samples without or with different prebiotics). SCFA content (acetate, propionate and butyrate) in the fermentation products ("Fermenta") 12 was analyzed by HPLC. TER was measured at t=0 h, t=4 h, t=18 h and t=24 h to monitor changes in the barrier integrity of the T84 monolayers. Non-limiting example of prebiotics include commercially available inulin and fructose oligosaccharides (FOS) that promote production of Butyrate by intestinal bacteria, galactose oligosaccharides (GOS) that promote growth of bifidobacteria in the intestine or prebiotics like resistant starch, corn arbionoxylan that promotes propionate. Other prebiotics may also be used.

We found that oligosaccharide fermentation by stool microbiota resulted in production of several types of SCFA (Table 2) and the amount produced of each individual SCFA and proportion of the three SCFA as a percentage differs among different oligosaccharides.

TABLE 2

| Prebiotic | Acetate (mM) | Propionate (mM) | Butyrate (mM) |
|-----------|--------------|-----------------|---------------|
| Blank 0 h | 0 | 0 | 0 |
| Blank 12 h | 11.04 | 21.32 | 2.63 |
| 0.5% Beads | 23.16 | 27.12 | 6.99 |
| 1.0% Beads | 17.88 | 21.53 | 5.67 |
| 1.5% Beads | 16.89 | 21.82 | 5.48 |
| Raw Potato Starch (RPS) | 16.49 | 22.03 | 4.51 |
| Fructo-oliogosaccharides (FOS) | 63.75 | 27.53 | 22.81 |
| Corn arabinoxylan (CAX) | 60.29 | 39.5 | 8.17 |

Figure 2:
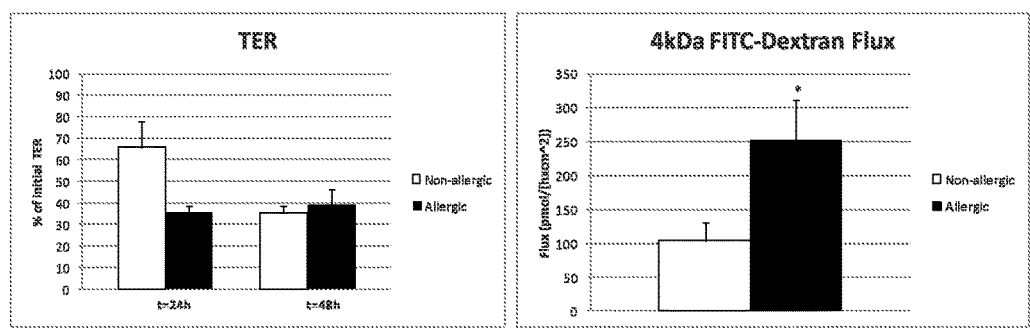
FIG. 2 shows the effect of the PMBC from patients with food allergy on TER of the T84 monolayer at indicated time points after start of co-culture with CD3/28-activated PBMC.

Furthermore, the magnitude of protective effects of these oligosaccharides for T84 loss of monolayer barrier that was induced by activated PBMC was significantly different and correlated with butyrate concentration in the fermentation product (FIG. 2). For example, it was found that NTX-1 prebiotic fiber, and corn arabinoxylan (CAX) (Nutrabiotix Corp, Lafayette, Ind.) and fructo-oligosaccharides (FOS) resulted in high production of butyrate when they were incubated with stool and their fermentation products protected T84 monolayer barrier leakiness induced by activated PBMC. These data showed that the in vitro bioassay is suitable to screen candidate prebiotics to see if they can protect intestinal epithelial cells against injurious agents and thus prevent gut leakiness. The assay also can determine if the candidate prebiotics can promote immune tolerance and anti-inflammatory effects through measurement of cytokines produced by PMBC. When unknown agents are screened to see whether they have prebiotic property and how the product impact microbiota composition, then microbiota composition of the stool is assessed before and after incubation with the agent using 16s DNA pyrosequencing method—an established and standard method of interrogating microbiota composition in stool.

Figure 3:
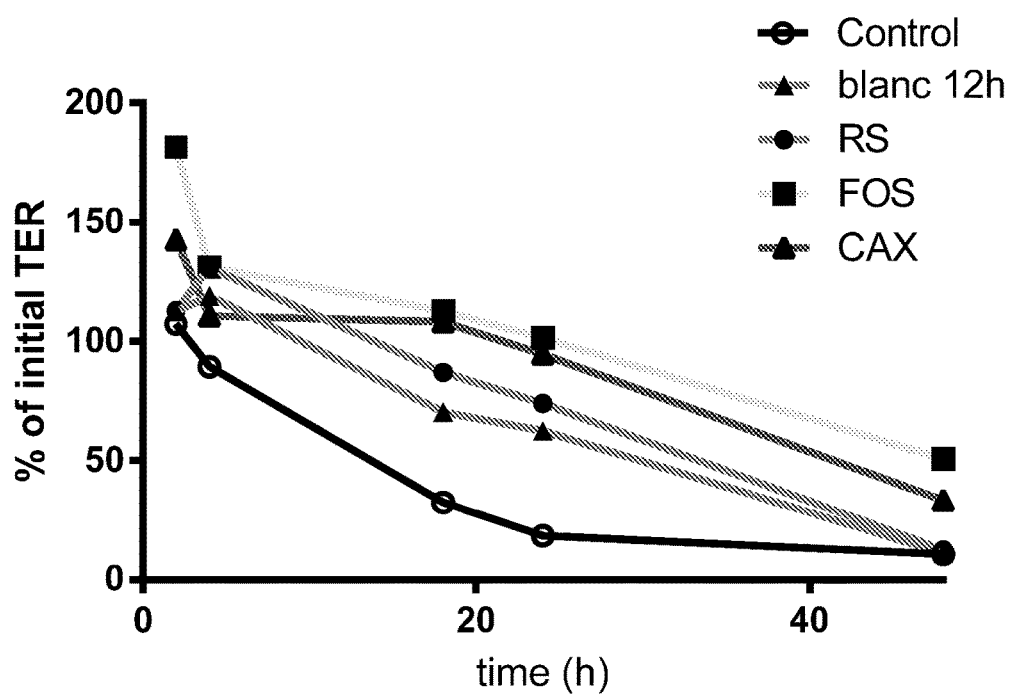
FIG. 3 shows that PBMC from patients with food allergy have increased capacity to disrupt epithelial barrier integrity. PBMC-induced disruption of intestinal epithelial barrier integrity can be prevented by exposure of T84 cells to Toll-like receptor 9 (TLR9) agonist. TLR9 is a receptor that recognizes bacterial DNA and thus TLR-9 agonist is to model the effects of prebiotic and will be used as "positive" control in the assay.
Figure 4:
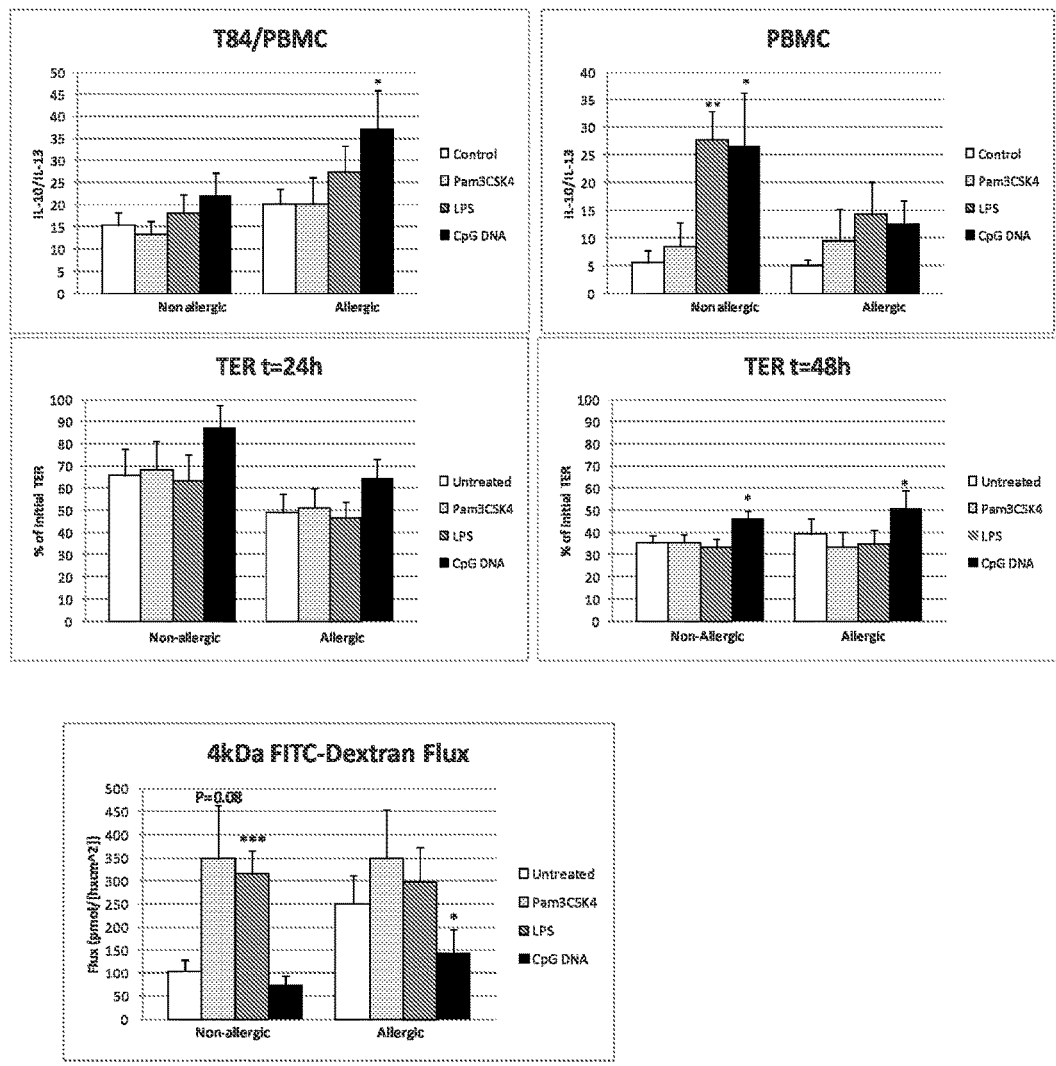
FIG. 4 shows that apical exposure of T84 cells to TLR9 agonist shifts the balance of the effector immune response away from the allergy-associated Th2 response, while promoting an anti-inflammatory environment.

The uniqueness of the assay is that stool and PBMC from a patient can be used in the assay to identify and choose the most suitable candidate prebiotics among a panel of prebiotic products. The feasibility of using PBMC from a diseased patient group has been demonstrated. In order to determine whether the in vitro bioassay is also suitable to screen candidate prebiotics in disease states and thus offer as a screen for personalized prebiotic treatment, the T84 monolayer was co-cultured with PBMC from patients with food allergies and the results showed that PBMC from food allergy cause more injury and leakiness of T84 monolayers (FIG. 2). When a TLR-9 agonist, commonly used to model changes in microbiota composition, was placed on the apical side of the T84 cells, the injurious effects of activated PBMC from food allergy patients was significantly blunted (FIG. 3). In Addition, exposure of T84 monolayers to the TLR9 agonist reversed the Th1/Th2 balance away from the allergic TH2 phenotype and promoted an anti-inflammatory environment (FIG. 4).

These Sets of Experiments Showed that the In Vitro Model System is Suitable to Screen Prebiotic Candidates in Patients.

PBMC-induced barrier disruption using a T84/PBMC co-culture system

Figure 5:
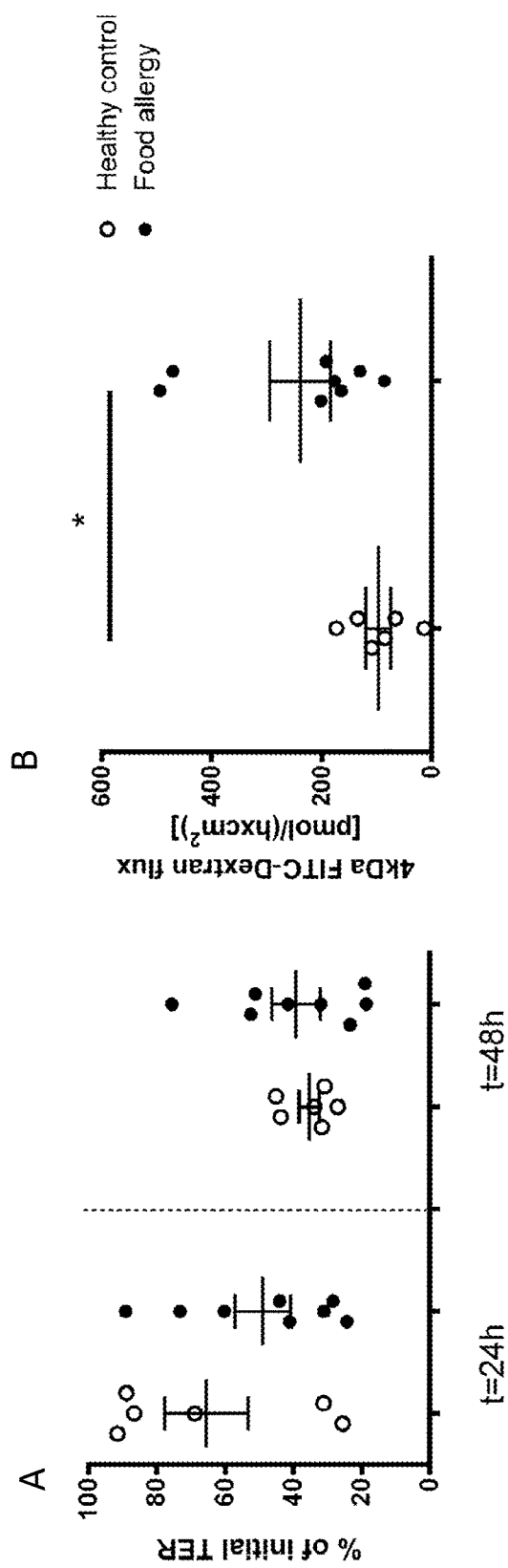
FIG. 5A-B. PBMC from food allergic subject have increased capacity to disrupt epithelial barrier integrity in vitro. PBMC from healthy controls or food allergic subjects were CD3/28-activated and co-cultured with T84 cells. TER (A) was measure after 24 h and 48 h of co-culture, and paracellular permeability (B) was assessed after 48 h of culture. Though no significant differences were observed on TER, PBMC from food allergic subjects caused an increased paracellular permeability of T84 monolayer to 4 kDa FITC-dextran. Data represent mean±SEM, *P<0.05.

First, the impact of activated PBMC activation of healthy controls and food allergic subjects on disruption of the barrier integrity of T84 cell monolayers to model a mucosal inflammatory response in vitro was evaluated. To this end, T84 cell monolayers were co-cultured with CD3/28-activated PBMC in the basolateral compartment for 48 h. TER was assessed after 24 h and 48 h after co-culture, followed by evaluation of paracellular permeability of the T84 monolayer to 4 kDa FITC-dextran. Co-culture of T84 monolayers with CD3/28-activated PBMC from healthy controls resulted in a 34.5% (P=0.037) and 64.5% reduction in TER (P<0.0001) after 24 h and 48 h of culture respectively. When using PBMC from food allergic subjects, a 51% (P=0.0057) and 60.7% reduction in the TER (P=0.0008) was observed after 24 h and 48 h of culture respectively. However, no difference in the TER was observed after 24 h or 48 h of co-culture between healthy controls and food allergic subjects (FIG. 5A). Though TER was equally reduced after 48 h of co-culture, T84 monolayers co-cultured with PBMC from food allergic subjects were significantly more permeable for 4 kDa FITC-dextran compared to T84 monolayers co-cultured with PBMC from healthy controls after 48 h of culture (FIG. 5B). Thus, PBMC-induced disruption of epithelial barrier integrity was faster and more severe with PBMCs from allergic subjects than with PBMCs from healthy subjects.

TLR Activation on IEC Modulates PBMC-Induced Barrier Disruption

Figure 6:
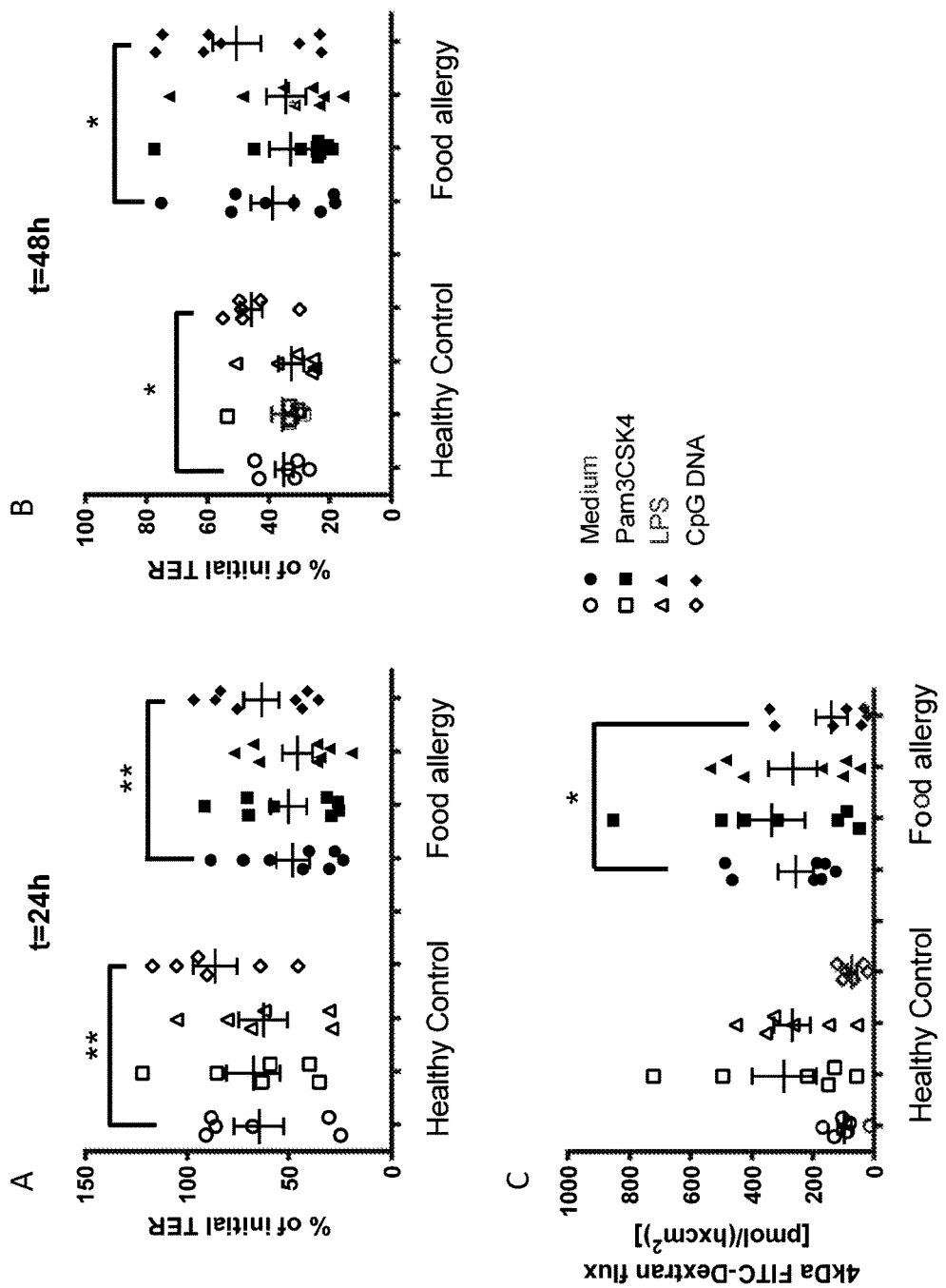
FIG. 6A-C. Apical TLR9 ligation on IEC reduces PBMC-induced barrier disruption of T84 monolayers. T84 cells were co-cultured with CD3/28-activated PBMC from healthy controls or food allergic subjects and simultaneously apically exposed to Pam3CSK4 (TLR2), LPS (TLR4) or CpG DNA (TLR9). TER was measured after 24 h (A) and 48 h (B) of co-culture, paracellular permeability (C) was assessed after 48 h of co-culture. Apical exposure of T84 monolayers to CpG DNA prevented PBMC-induced barrier disruption for both healthy controls and food allergic patients after 24 h of culture. This effect persisted after 48 h of culture. In addition, apical TLR9 ligation on IEC reduced epithelial permeability when using PBMC from food allergic patients. Data represent mean±SEM, *P<0.05, **P<0.01.

Next, we evaluated whether apical exposure of T84 cell monolayers to TLR ligands during co-culture with CD3/28-activated PBMC affect barrier integrity of IEC. To this end, T84 cells were apically exposed to ligands for TLR2 (Pam3CSK4), TLR4 (LPS) or TLR9 (CpG DNA). Apical exposure of T84 cells to CpG DNA increased the TER compared to medium controls to a similar extent for both healthy controls and food allergic subjects (FIGS. 6A and 6B). In parallel, apical TLR9 activation reduced the permeability of T84 cell monolayers induced by PBMC from food allergic subjects compared to medium controls (FIG. 6C). Ligation of TLR2 and TLR4 did not affect TER of T84 cells upon co-culture with PBMC from healthy controls or food allergic subjects. However, in healthy controls, TLR2 and TLR4 ligation on IEC increased the permeability of the T84 monolayers to 4 kDa FITC-dextran. These data suggest that apical TLR9 activation on IEC may contribute to the maintenance of homeostasis in the gut mucosa by supporting epithelial barrier integrity and thereby preventing allergic inflammation.

Figure 7:
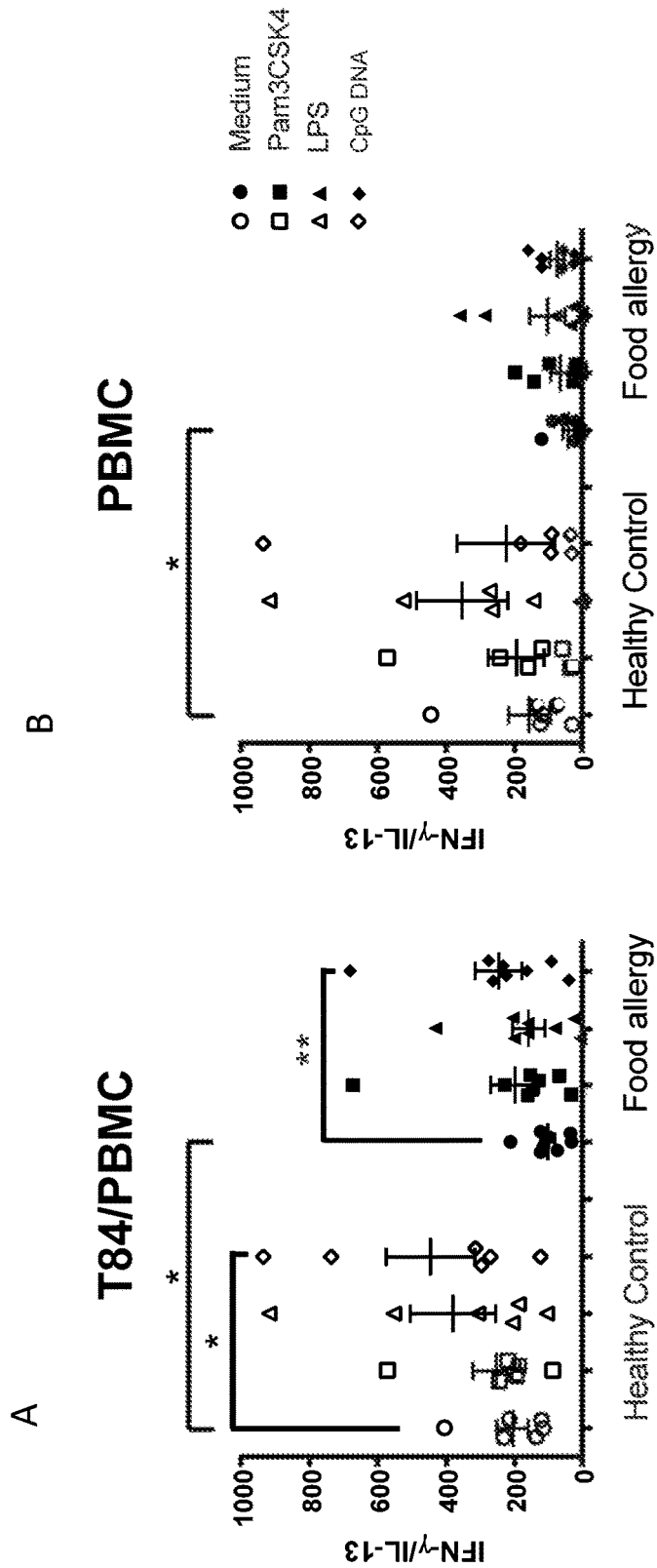
FIG. 7A-B. Apical TLR9 ligation on IEC enhances a $T_h1$ polarized effector response. T84 cells were co-cultured with PBMC from healthy controls or food allergic subjects. TLR ligands were added in the apical compartment of T84/PBMC co-cultures (A) or added to PBMC cultures in the absence of T84 cells (B) and production of IFN-γ and IL-13 was assessed after 24 h of culture. PBMC from food allergic subjects showed a reduced IFN-γ/IL-13 ratio, indicating a $T_h2$-polarized response upon CD3/28-activation. CpG DNA enhanced the IFN-γ/IL-13 ratio only in the T84/PBMC co-cultures, for both healthy controls and food allergic subjects. Data represent mean±SEM, *P<0.05.

TLR9 Activation on IEC shifts the $T_h1/T_h2$ Balance Towards a $T_h1$ Type Effector Response To evaluate whether epithelial TLR ligation modulates cytokine production by the PBMC, basolateral supernatants were collected 24 h after co-culture. Exposure of CD3/28-activated PBMC in the absence of IEC to TLR ligands served as a control to evaluate the contribution of IEC in modulating the cytokine production by PBMC. First we evaluated the production of IFN-γ and IL-13 as a reflection of a $T_h1$ and $T_h2$ type effector response (Table 3). No significant changes in the production of IFN-γ or IL-13 were observed, though IFN-γ production by the PBMC from food allergic subjects tended to be lower in T84/PBMC co-cultures (P=0.093). However, the IFN-γ/IL-13 ratio was significantly reduced in T84/PBMC co-cultures when comparing food allergic subjects to healthy controls, indicating that PBMC from food allergic subjects show a $T_h2$-skewed effector response (FIGS. 7A and 7B). Interestingly, apical exposure of T84/PBMC co-cultures to CpG DNA increased the IFN-γ/IL-13 ratio for both PBMC from healthy and food allergic subjects (FIG. 7A). This was not observed when PBMC were stimulated with CpG DNA in absence of T84 cells (FIG. 7B).

Apical TLR9 Activation on IEC Supports an Anti-inflammatory Milieu

Figure 8:
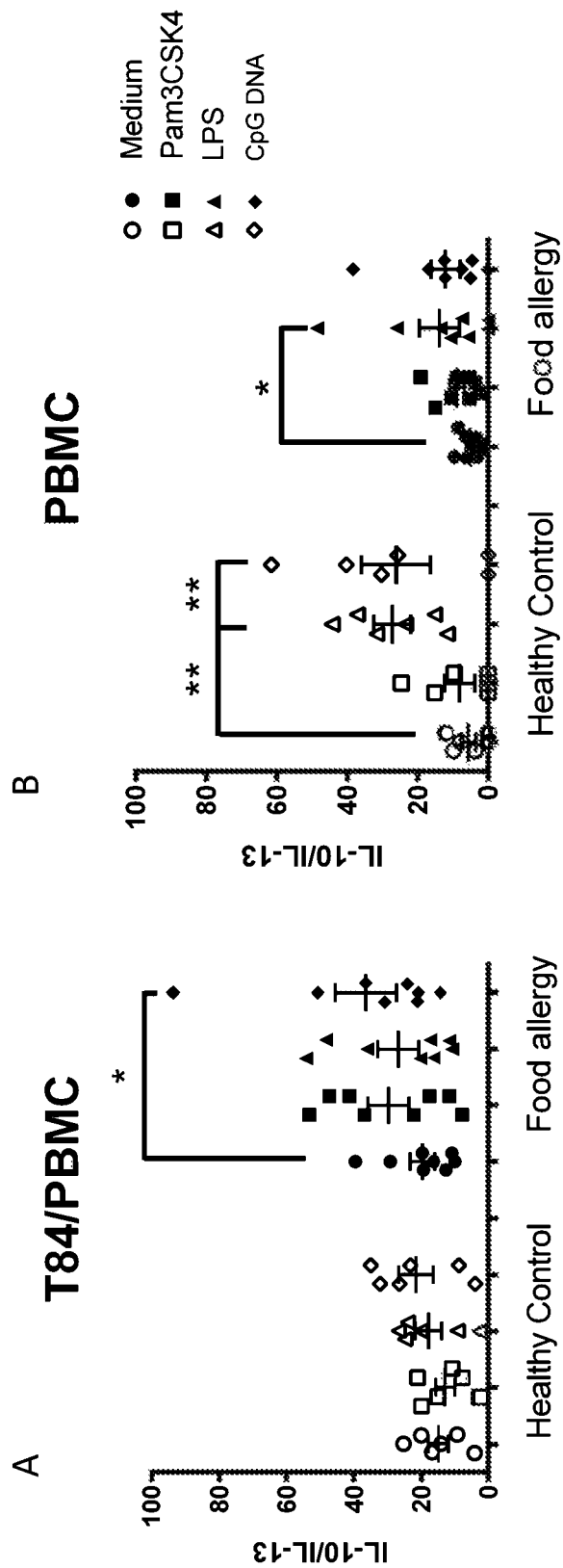
FIG. 8A-B. Apical TLR9 ligation on IEC enhances a $T_h1$ polarized effector response. T84 cells were co-cultured with PBMC from healthy controls or food allergic subjects. TLR ligands were added in the apical compartment of T84/PBMC co-cultures (A) or added to PBMC cultures in the absence of T84 cells (B) and production of IFN-γ and IL-13 was assessed after 24 h of culture. PBMC from food allergic subjects showed a reduced IFN-γ/IL-13 ratio, indicating a $T_h2$-polarized response upon CD3/28-activation. CpG DNA enhanced the IFN-γ/IL-13 ratio only in the T84/PBMC co-cultures, for both healthy controls and food allergic subjects. Data represent mean±SEM, *P<0.05.

In addition to analyzing the $T_h1/T_h2$ balance, we also addressed whether apical TLR9 activation of IEC supports an anti-inflammatory microenvironment by measuring the levels of IL-10 (Table 3). Though no differences in IL-10 production were observed, the IL-10/IL-13 ratio tended to increase upon apical exposure of T84 cells to CpG DNA co-cultured with healthy donor PBMC (P=0.091), whereas the IL-10/IL-13 ratio was significantly increased when PBMC from food allergic patients were used (FIG. 8A). In addition, the IL-10/IFN-γ was not affected upon apical exposure of IEC to CpG DNA (0.11±0.05 vs. 0.12±0.06 for healthy controls, 0.21±0.04 vs. 0.19±0.06 in food allergic subjects). In the absence of T84 cells, both LPS and CpG DNA stimulation enhanced the IL-10/IL-13 ratio when using PBMC from healthy controls. LPS stimulation of PBMC from food allergic subjects also resulted in an increased IL-10/IL-13 ratio, while stimulation with CpG DNA did not affect the IL-10/IL-13 (FIG. 8B).

Pro-inflammatory Cytokine Production by PBMC is Suppressed Upon Apical Exposure of IEC to CpG DNA

TABLE 3

| | | T84/PBMC | | | | PBMC |
|---|---|---|---|---|---|---|
| | | Medium | Pam3CSK4 | LPS | CpG DNA | Medium |
| IL-6 | HC | 7736 ± 1411## | 7209 ± 1531 | 9040 ± 2424 | 7291 ± 1376 | 3294 ± 1082 |
| | FA | 8397 ± 2096## | 5968 ± 1324** | 7410 ± 2112 | 6400 ± 1671* | 4159 ± 1284 |
| IL-8 | HC | 25069 ± 5163# | 23052 ± 5527 | 23124 ± 5683 | 20758 ± 5247** | 36019 ± 4778 |
| | FA | 20461 ± 5605 | 16854 ± 4954 | 17103 ± 4334 | 15733 ± 4509* | 27055 ± 4956 |
| IL-10 | HC | 658 ± 98.6 | 581.1 ± 110.7 | 632.7 ± 125.1 | 652.8 ± 105.5 | 194.5 ± 93.8 |
| | FA | 826.7 ± 205.5 | 853.3 ± 212.9 | 777.6 ± 163.2 | 834 ± 233.6 | 351.4 ± 120.1 |
| IL-13 | HC | 37.3 ± 9.2 | 37.8 ± 9.2 | 31.3 ± 9.1 | 27.5 ± 7.5* | 69.2 ± 26.1 |
| | FA | 44.3 ± 11.6 | 40.8 ± 12.1 | 33.8 ± 11.0** | 35.9 ± 10.5** | 72.3 ± 17.1 |
| IFN-γ | HC | 11188 ± 3810 | 8614 ± 2455 | 10392 ± 2967 | 10731 ± 3289 | 5156 ± 1535 |
| | FA | 5273 ± 1850 | 6533 ± 2125 | 4390 ± 1700 | 7040 ± 2454 | 2815 ± 1037 |
| TNF-α | HC | 3068 ± 606# | 3073 ± 509 | 2928 ± 712 | 2531 ± 552* | 1489 ± 286 |
| | FA | 2411 ± 514## | 2251 ± 534 | 2403 ± 516 | 2092 ± 493** | 1151 ± 320 |

| | | PBMC | | |
|---|---|---|---|---|
| | | Pam3CSK4 | LPS | CpG DNA |
| IL-6 | HC | 9472 ± 2153* | 12399 ± 2174** | 2564 ± 824 |
| | FA | 8073 ± 2055** | 9909 ± 2073*** | 5940 ± 2450 |
| IL-8 | HC | 43737 ± 2856 | 43034 ± 2960 | 19912 ± 2430** |
| | FA | 32940 ± 4869 | 35682 ± 4770* | 25420 ± 6779 |

TABLE 3-continued

| | | | | |
|---|---|---|---|---|
| IL-10 | HC | 254.7 ± 135.4 | 545.4 ± 134.7* | 391.9 ± 149.3 |
| | FA | 422.8 ± 98.6 | 586 ± 159.4*** | 477.3 ± 157.7* |
| IL-13 | HC | 59.2 ± 17.0 | 28.3 ± 8.7* | 19.5 ± 3.8* |
| | FA | 59.4 ± 15.2 | 34.0 ± 10.7*** | 39.9 ± 12.8*** |
| IFN-γ | HC | 5663 ± 1768 | 6070 ± 2282 | 2394 ± 966 |
| | FA | 2824 ± 1163 | 2188 ± 908 | 3945 ± 1543 |
| TNF-α | HC | 2206 ± 1155 | 2607 ± 1165* | 1024 ± 213* |
| | FA | 979.1 ± 244 | 945.4 ± 294 | 1199 ± 437 |

Cytokine levels are in pg/mL and data are shown as mean ± SEM. (HC, healthy control; FA, food allergy.)
*$P < 0.05$ compared to medium control.
**$P < 0.01$ compared to medium control.
***$P < 0.001$ compared to medium control
$P < 0.05$ compared to medium control using PBMC in absence of T84 cells.
$P < 0.01$ compared to medium control using PBMC in absence of T84 cells.

We also measured the production of the pro-inflammatory cytokines IL-6, IL-8 and TNF-α by PBMC from both healthy controls and food allergic subjects in the T84/PBMC co-culture model (Table 3). T84 cells enhanced the production of IL-6 and TNF-α, and reduced IL-8 secretion in T84/PBMC co-cultures using PBMC from healthy controls. Similar observations, with the exception of IL-8, were made when using PBMC from food allergic subjects in the co-culture model. Apical ligation of TLR9 on T84 cells suppressed the production of IL-6, IL-8 and TNF-α by PBMC from both healthy controls and food allergic subjects (Table 3). Although direct stimulation of PBMC using CpG DNA from healthy controls also reduced pro-inflammatory cytokine production, TLR9 activation on PBMC from food allergic subjects did not suppress the production of IL-6, IL8 and TNF-α. These data suggest that apical TLR9 on IEC activation is required to support an anti-inflammatory microenvironment in food allergy.

The use of stool and PBMC from healthy subjects is suitable for screening candidate prebiotic products to see if they have any gut health promoting properties (change in microbiota composition, change in microbiota function like fermentation profile, increase in production of SCFA, restoration of intestinal epithelial barrier integrity, change in immune response and promotion of immune tolerance). But, use of PMBC and stool from healthy subjects is not suitable for selecting the suitable known prebiotics in order to offer personalized treatment for patients. To this end, stool from a given patient is incubated with series of candidate prebiotics and fermentation products are collected, passed through a microfilter and placed on the apical side of T84 monolayers. PBMC from the same patient will be placed on basolateral side of the monolayer and activated and cultured for 24 hours. Monolayer barrier (TER and FITC dextran) and cytokine levels are assessed in the culture media. Microbiota composition will also be characterized. In some embodiments, the microbiota composition will be characterized using 16s DNA pyrosequencing method in the stool before and after incubation with prebiotics. The optimal prebiotic is the one that is most protective of monolayer integrity and most effectively blunted production of pro-inflammatory cytokines (e.g. TNF, IL-1, IL-6, IL-17, IL-8, IL-10, IL-13).

A feature of the bioassay using the T84 monolayer and PBMC's is that it is inexpensive and is suitable for high throughput method for the initial step for the screening of candidate potential prebiotic products and choice of right prebiotic for a given subject. However, the T84 cells are a cell line which is different from an individual patient's intestinal epithelial cells. In some embodiments, an individual patient's epithelial cells may be used to in the bioassay. Recent advances in intestinal epithelial cell biology has made it possible to make organoid cultures, a technique in which a 'minigut' is created out of the patient's intestinal stem cells collected from a small biopsy taken during routine endoscopy, such as upper endoscopy (EGD) to obtain small bowel biopsy or sigmoidoscopy to obtain colonic biopsy samples. In combination with the collected stool and PBMC from the same patient, this alternative model provides a screen for the effect of prebiotic oligosaccharides in a system which consists entirely of patient-derived samples. However, due to expense and longer time to turn around the result, this fully personalized bioassay will be reserved for the second step screening to choose highly selective prebiotic products for a given patient with a specific disease and specially for those with diseases where there is abnormal intestinal epithelial function (e.g. IBD and Parkinson's disease).

Method for In Vitro Fecal Fermentation and Metabolite Analyses for Measuring Short Chain Fatty Acids.

Batch fecal fermentation was performed as per the method of Lebet et al (1998b) with some minor modifications (Rose et al 2010a). All the steps were performed under constant carbon dioxide purging. Each substrate was weighed in 3 test tubes for each time point such that all the analysis occurred in triplicate. In brief, a carbonate-phosphate buffer of pH 6.8±0.1 was prepared and autoclaved. This neutral pH buffer has been used by a number of other researchers (Sanz et al 2005; Edwards et al 1996; Roberfroid et al 1998). While cooling the buffer, cysteine (0.1 g/mL) was added as a reducing agent (2.5 mL/L buffer). Hydration of samples (50±0.5 mg equivalent carbohydrate) was performed for 16 h at 4° C. by adding 4 mL of carbonate-phosphate buffer and 100 μL Oxyrase for Broth (Oxyrase Inc., Mansfield, Ohio, U.S.A.), which was added to remove oxygen from the microenvironment of the test tube. Following hydration, samples were equilibrated at room temperature for 2 h. Fecal samples were collected from 3 healthy adults and the fecal inoculum was prepared by pooling the samples. All 3 subjects were on their routine diet and had not taken antibiotics within the previous 6 mo. Fecal samples were collected in plastic bags that were sealed after escaping the air, transported on ice, and used within 2 h of collection. The inoculum comprised feces and freshly prepared carbonate-phosphate buffer in a ratio of 1:3 (w/v). The mixture was homogenized in a household blender for 1 min and strained through 4 layers of cheese cloths. Substrates were then inoculated under a stream of carbon dioxide with 1 mL of fecal slurry. Test tubes without the substrate were used as blanks at each measurement time. After rinsing the headspace of each test tube with carbon dioxide, they were sealed and incubated at 37° C. in a shaking water bath. After 4, 8, 24, and 48 h of fermentation, designated tubes were removed from the water bath and fermentation was terminated by adding 400 µL of copper sulphate solution (2.75 mg/mL). The final volume of the batch culture was 5.5 mL. Gas production was measured using graduated syringe displacement and pH of the samples was measured using a standard pH meter (Orion Research Inc., Boston, Mass., U.S.A.).

For SCFA analysis, 800 µL of the fecal slurry were combined with 200 µL of a mixture containing 50 mM 4-methyl-valeric acid (nr 277827-5G, Sigma-Aldrich Inc., St. Louis, Mo., U.S.A.), 5% meta-phosphoric acid, and copper sulfate (1.56 mg/mL) and stored at −40° C. until analysis. Later, defrosted tubes were centrifuged (3000×g, 10 min) and 200 µL was transferred into GC vials, and then injected into a Hewlett Packard model 5890 Series II gas chromatograph (Hewlett Packard, Palo Alto, Calif., U.S.A.). SCFA were separated on a fused silica capillary column (Nukol™, Supelco nr 40369-03A, Bellefonte, Pa., U.S.A.). Identification and flame ionization detector (FID) response factors for acetate, propionate, and butyrate relative to 4-methylvaleric acid were calculated by injecting a volatile acid standard mix (Supelco, Bellefonte, Pa., U.S.A.). Quantification was accomplished by measuring the peak areas for acetate, propionate, and butyrate relative to 4-methylvaleric acid.

Method for interrogating Microbiota in the Stool Before and After Fermentation.

Microbial Community Analysis. Genomic DNA is obtained using an extraction kit according to manufacturer's instructions (MP Biomedicals FastDNA SPIN Kit for Soil, #116560200). Genomic DNA samples are then amplified and sequenced for fragments of bacterial small subunit (SSU or 16S) ribosomal RNA (rRNA) genes. Briefly, PCR amplification is performed using the primers Gray28F and Gray519r [1] and sequencing reactions are performed on a Roche 454 FLX instrument (Roche, Indianapolis, Ind.) with Titanium reagents, titanium procedures, a one-step PCR, and a mixture of Hot Start and Hot Star high-fidelity Taq polymerases. After sequencing, all failed sequence reads and low-quality sequences are removed, and sequences are depleted of any nonbacterial ribosome sequences and chimeras using custom software [2], as described previously [3]. Clustering sequences into taxonomic groups from species to phylum is performed with the software package USEARCH [4], and taxonomic affiliation of sequences is performed by query of representative sequences against a curated 16S rRNA gene database.

For determination of diversity, raw sequences are quality filtered at a Q20 level within the software package CLC genomics workbench (CLC bio, Denmark), and sequences shorter than 275 bases are removed. Subsequently, each sample set is randomly sub-sampled to the same number of sequences (800 sequences/sample, ~75% of the smallest library) to allow for direct comparison of calculated diversity indices. Sequences, from each sample, are pooled and processed through the Ribosomal Database Project's (RDP) Pyrosequencing pipeline [5] (http://pyro.cme.msu.edu/). Briefly, all sequences are aligned, and clustered using a 0.03 similarity threshold for complete linkage clustering. The number of sequences from each sample cluster is identified and a biological observation matrix (BIOM) is generated [6]. The BIOM is analyzed using the software package Primer6 (v6.1.15; PrimerE). Univariate diversity analysis (i.e., Shannon index) is implemented using the DIVERSE function in Primer6.

Species-Taxonomic affiliation of clustered sequence data is determined as described above, and the data is used to generate multiple BIOMs at multiple taxonomic levels, including species, genus and family. The BIOMs are subsequently used for analysis of microbial community structure and statistical analyses. For hypothesis testing, species-level data organized in a BIOM are pre-treated to standardize taxon abundance within each sample, and the data is subsequently square-root transformed to down-weight the impact of high abundance species. The transformed data is then used to generate a pair-wise resemblance matrix based on Bray-Curtis similarity (Primer6) that is analyzed using hierarchical clustering (group average) and non-metric multi-dimensional scaling (NMDS). Analysis of similarities (ANOSIM) is used to determine statistically significant changes in microbial community structure in a priori defined sample grouping. To do so, a test statistic "R" is calculated from the average distance of all members of a group and contrasted with average distances between replicates of different groups. The R statistic is calculated so that R=1 if all replicates within groups are more similar than any replicates from different samples and R values approaching zero indicate dissimilarity. To determine significance, the R statistic is calculated under permutations of the sample labels, and the measured R value is compared to the permutation distribution [7]. Similarity percentage for each group (5-10/group) was independently analyzed. Community dissimilarity between treatment groups is calculated using the 'similarity percentages' (SIMPER) function within Primer6, employing resemblance based on Bray Curtis similarity.

Treatment effects are also analyzed at higher taxonomic level, employing a BIOM generated from family-level clustered sequence data. Principal coordinates analysis (PCA) is performed within the software package Canoco (v5) [8]. Data is standardized by sample, and log-transformed prior to PCA.

Other objects, features and advantages of the present invention are apparent from the detailed description. Although the instant invention describes preferred and alternate embodiments that will be used for screening prebiotics for their efficacy in preventing and/or treating disease in a patient, it is contemplated that the instant invention can be used in the screen of any compound or composition that could be efficacious in reducing gut leakiness or inflammation. Thus, the instant disclosure should not be read to limit the use of the instant invention to screen for prebiotics but for probiotics, biological and compounds that can be used to treat a patient. Furthermore, the organization and type of the individual elements of the assay represent preferred embodiments and should not be read to limit the use of alternate configurations and types. One of ordinary skill in the art can discern, from the description of the instant invention, alternate embodiments that can be contemplated by the designers of the dual cell screen.

REFERENCES

1. Ishak H D, Plowes R, Sen R, Kellner K, Meyer E, Estrada D A, Dowd S E, Mueller U G (2011) Bacterial diversity in *Solenopsis invicta* and *Solenopsis geminata* ant colonies characterized by 16S amplicon 454 pyrosequencing. Microb Ecol 61: 821-831. 10.1007/s00248-010-9793-4 [doi].

2. Gontcharova V, Youn E, Wolcott R D, Hollister E B, Gentry T J, Dowd S E (2010) Black Box Chimera Check (B2C2): a Windows-Based Software for Batch Depletion of Chimeras from Bacterial 16S rRNA Gene Datasets. Open Microbiol J 4: 47-52. 10.2174/1874285801004010047 [doi].

3. Acosta-Martinez V, Dowd S, Sun Y, Allen V (2008) Tag-encoded pyrosequencing analysis of bacterial diversity in a single soil type as affected by management and land use. Soil Biology & Biochemistry 40: 2762-2770.

4. Edgar R C (2010) Search and clustering orders of magnitude faster than BLAST. Bioinformatics 26: 2460-2461. btq461 [pii]; 10.1093/bioinformatics/btq461 [doi].

5. Cole J R, Wang Q, Cardenas E, Fish J, Chai B, Farris R J, Kulam-Syed-Mohideen A S, McGarrell D M, Marsh T, Garrity G M, Tiedje J M (2009) The Ribosomal Database Project: improved alignments and new tools for rRNA analysis. Nucleic Acids Res 37: D141-D145. gkn879 [pii]; 10.1093/nar/gkn879 [doi].

6. McDonald D, Clemente J C, Kuczynski J, Rideout J R, Stombaugh J, Wendel D, Wilke A, Huse S, Hufnagle J, Meyer F, Knight R, Caporaso J G (2012) The Biological Observation Matrix (BIOM) format or: how I learned to stop worrying and love the ome-ome. Gigascience 1: 7. 2047-217X-1-7 [pii]; 10.1186/2047-217X-1-7 [doi].

7. Clarke, K. R. and Warwick, R. M. (2001) Change in Marine Communities: An Approach to Statistical Analysis and Interpretation. Plymouth Marine Laboratory, UK: Primer-E Ltd.

8. Braak C J F, Smilauer P (2002) CANOCO Reference Manual and CanoDraw for Windows User's Guide: Software for Canonical Community Ordination (version 4.5). 1-500.

9. S. de Kivit, E. van Hoffen, N. Korthagen, J. Garssen, and L. E. Willemsen, Apical TLR ligation of intestinal epithelial cells drives a Th1-polarized regulatory or inflammatory type effector response in vitro. Immunobiology 216 (2011) 518-27.

The invention claimed is:

1. A method of identifying a prebiotic to treat a subject in need thereof to promote intestinal barrier integrity or to blunt an inflammatory response, the method comprising:
 a) co-culturing an epithelial cell layer and a subject sample;
 b) adding a fermentation product to the co-culture;
 c) adding a prebiotic to the co-culture;
 d) culturing the prebiotic and the fermentation product together with the co-culture for a period of time;
 e) measuring a readout of step (d);
 f) culturing the fermentation product together with the co-culture and without the prebiotic for a period of time;
 g) measuring a readout of step (f);
 h) comparing the readouts from steps (e) and (g); and
 i) identifying an increase in intestinal barrier integrity or a decrease in an inflammatory response by the comparison of the readouts from steps (e) and (g), to identify the prebiotic with which to treat the subject.

2. The method according to claim 1, wherein the readouts in steps (e) and (g) are determined by measuring the integrity of the epithelial cell layer or a level of a cytokine.

3. The method according to claim 1, wherein the fermentation product is a stool sample, and further comprising fermenting the stool sample and the prebiotic together prior to adding the fermentation product to the co-culture.

4. The method according to claim 1, comprising adding the subject sample to the basolateral side of the epithelial cell layer.

5. The method according to claim 1, comprising measuring the readout comprising a transepithelial electrical resistance of the co-culture.

6. The method according to claim 1, comprising measuring the readout comprising fluorescein isothiocyanate-dextran (FITC Dextran) flux across the epithelial cell layer to determine intestinal barrier integrity.

7. The method according to claim 1. wherein the readouts in steps (e) and (g) are determined by measuring the amount of a cytokine selected from the group consisting of TNF, IL-1, IL-6, IL-17, IL-8, IL-10, IL-13 and combinations thereof.

8. The method according to claim 1, further comprising comparing the readouts from testing a plurality of co-cultures from the subject, wherein each of the plurality of co-cultures is tested by incubation with a different prebiotic or combination of prebiotics.

9. The method according to claim 1, comprising fermenting the fermentation product about 12 hours or more before adding the fermentation product to the co-culture.

10. The method according to claim 9, comprising fermenting the fermentation product together with the prebiotic.

11. The method according to claim 1, comprising adding the fermentation product to an apical side of the epithelial cell layer.

12. The method according to claim 1, wherein the fermentation product comprises a stool sample from the subject.

13. The method according to claim 1, wherein the subject cell sample comprises peripheral blood mononuclear cells.

14. The method according to claim 1, wherein the epithelial cell layer is a cell line or cells from the subject.

15. The method according to claim 14, wherein the epithelial cell layer comprises intestinal organoids from the subject.

* * * * *